United States Patent [19]

Deutsch

[11] 4,147,480
[45] Apr. 3, 1979

[54] ASYMMETRIC PERMEABLE MEMBER

[76] Inventor: Daniel H. Deutsch, 141 Kenworthy Dr., Pasadena, Calif. 91105

[21] Appl. No.: 825,947

[22] Filed: Aug. 19, 1977

[51] Int. Cl.² .......................................... F04B 39/00
[52] U.S. Cl. ................................................ 417/572
[58] Field of Search ..................... 417/53, 207, 572; 73/23, 28

[56] References Cited

U.S. PATENT DOCUMENTS

| | | | |
|---|---|---|---|
| 3,150,818 | 9/1964 | Schumacher | 417/207 |
| 3,286,531 | 11/1966 | Shapiro et al. | 417/572 X |
| 3,565,551 | 2/1971 | Hobson | 417/53 X |
| 3,693,457 | 9/1972 | Pilat | 73/28 X |
| 3,795,135 | 3/1974 | Anderson | 73/28 |
| 3,837,762 | 9/1974 | Lee | 415/207 |

*Primary Examiner*—Carlton R. Croyle
*Assistant Examiner*—Edward Look
*Attorney, Agent, or Firm*—Edgar W. Averill, Jr.

[57] ABSTRACT

A member for causing the circulation of a gas therethrough. The asymmetric member has numerous shaped pores through it such that the absolute effusional resistance to gas flow is anisotropic. The member is useful in causing the circulation of gases.

98 Claims, 14 Drawing Figures

ASYMMETRIC PERMEABLE MEMBER

BACKGROUND OF THE DISCLOSURE

The circulation of fluids through open and closed systems has many applications in the arts, sciences and technology. Mechanical reciprocating pumps, centrifugal pumps, undulating tubes, thermal gradients and fans are all commonly used to move fluids. One particular application where the above listed circulating systems are often impractical is in bacteriological research where a sterile flask has a plug of cotton or other porous substance in the neck thereof and ambient air or other gas is allowed to pass through the cotton. For many reactions such as fermentation reactions the rate at which the air passes through the cotton is an important factor which determines the rate at which the reaction takes place.

A major shortcoming of the use of a cotton plug in the sterile shake flask is the very slow rate of gas exchange through the cotton plug. Consequently, the gas exchange through the cotton plug is rate limiting rather than the biological process in the bacteriological medium. Elaborate sterile gas pumping systems have been developed and used to increase the rate of air throughput. However, such systems are quite expensive, difficult to operate and maintain and provide a source of possible contamination. Some bacteriological processes are carried out under reduced pressure or elevated pressure and reactions are also carried out in the presence of a particular gas.

More particularly, the forced flow of gases has typically utilized mechanical compressors or other devices which can give rise to impurities caused by the necessary presence of lubricants. The need for moving gases in highly purified conditions has made most mechanical systems impractical. Furthermore, many gases are not compatible with the common materials of construction and thus can not be pumped by conventional devices. Still further, some processes require elevated temperatures or reduced temperatures. Systems for circulating air or other gases is made more difficult by the presence of such conditions.

SUMMARY OF THE INVENTION

It is thus an object of the present invention to provide a gas circulating system which is simple to use, inexpensive to maintain and yet effective to increase the flow of gas through a chamber.

It is another important object of the present invention to provide a gas circulating system useful for depolluting industrial smoke stack gases.

It is a still further object of the present invention to provide a gas circulating system which consumes no energy.

The circulating system of the present invention comprises at least one hollow member, which has at least one end open, fabricated from a relatively gas impermeable material. The hollow member is sealed, gas tight, across a chamber which has two sets of conduit ports, an inlet set of conduit ports and an outlet set of conduit ports, such that the two sets of conduit ports are separated by the wall of the hollow member, and the only flow of gas through the chamber must take place through the wall of the hollow member. The afore described assemblage will be called an activating unit. The wall of the hollow member has a thickness of less than about 3 millimeters and greater than about 0.001 micron. The wall of the hollow member contains a plurality of tapered holes passing between the surfaces of the wall. The smaller openings of the holes through the wall are substantially all either in unison on the outside surface of the wall of the hollow member or in unison on the inside surface of the wall of the hollow member, with the smaller openings on the inside surface the generally preferred embodiment. These tapered holes may be uniform in size and shape or they may be irregular. The tapered holes also may be highly branched and interconnected. The tapered holes may also be flared at the larger openings. The distance across the smaller openings of the tapered holes is less than three times the mean free path of the gas molecules which is to be employed in this gas circulating system under the operating conditions of pressure and temperature. The hollow member, the chamber and the conduit ports are all both chemically and physically stable to the gas and of a relatively nonvolatile nature under the operating conditions of temperature and pressure which are to be used. The mean absolute effusional resistance coefficient, $\xi$, of the wall of the hollow member is greater than $10^{-4}$ and less than 2.0 under the operating conditions in the said chamber. When the said activating unit is filled with a gas to the operating pressure and at the operating temperature, the operating gas is urged through the wall of the hollow member, through the chamber and through the inlet and outlet conduit parts. The operating activating unit described above will be referred to as an aerator.

Some characteristics of the asymmetric gas-pervious hollow member may be set forth by a series of equations set forth below wherein:

$R_i$ = the absolute effusional resistance of the wall of the hollow member to the gas in the first direction, from said "i" of the wall of the hollow member to side "ii" of the wall of the hollow member (see FIG. 7 of the drawing discussed below).

T = the absolute temperature, °K, of the gas adjacent to the hollow member.

$P_i$ = the pressure of the gas on side "i" of the wall of the hollow member.

d = thickness of the wall of the hollow member.

A = the wall area of the hollow member.

Q = the net gas flow rate through the wall of the hollow member.

$R_{ii}$ = the absolute effusional resistance of the wall of the hollow member to the gas in the second direction, from side "ii" of the wall of the hollow member to side "i" of the wall of the hollow member.

$P_{ii}$ = the pressure of the gas on the side "ii" of the wall of the hollow member.

When the gas pressure is set so that $P_i$ is the operating pressure on side "i" at T °K, and at the same time $P_{ii}$ is held near zero Torr so that $P_i$ is much greater than $P_{ii}$, $R_i$ is defined by Equation (1)

$$R_i = AP_i/Qd \qquad \text{Eq. (1)}$$

and correspondingly when the gas pressure is set so that $P_{ii}$ is the operating pressure on side "ii" at T °K, and at the same time $P_i$ is held near zero Torr so that $P_{ii}$ is much greater than $P_i$, $R_{ii}$ is defined by Equation (2).

$$R_{ii} = AP_{ii}/Qd \qquad \text{Eq. (2)}$$

When for a particular hollow member with a given gas and at a temperature, T °K, if $R_1$ and $R_{ii}$, the absolute effusional resistance of the given hollow member in the two opposite directions, as calculated from Equations (1) and (2) respectively are not equal under conditions where $P_i$ and $P_{ii}$ in Equations (1) and (2) respectively are equal, then the hollow member's absolute effusional resistance is anisotropic for those specific operating conditions.

The hollow member's mean absolute effusional resistance coefficient, $\xi$, is defined by Eq. (3)

$$\xi = \left| \frac{2(R_i - R_{ii})}{R_i + R_{ii}} \right| \qquad \text{Eq. (3)}$$

and $\xi$ is a measure of the hollow member's anistropy. For a given single asymmetric gas-pervious hollow member and a given gas under specified temperature and pressure, the mean absolute effusional resistance coefficient $\xi$ must be greater than $10^{-4}$ and less than 2.0, and may have intermediate values such as 0.01.

The tapered holes through the wall of the hollow member are of such a size that the diameter of the openings of the holes at the smaller end are less than about three (3) times the means free path of the molecules of the gas under the conditions employed and greater than the mean diameter of the molecules of the gas, with approximately one tenth to one fiftieth of the mean free path of the gas molecules a typical useful range and where the gas molecules pass through the smaller end of the tapered holes by effusion.

As referred to herein the term "aerator" will be used to denote a gas circulating device which causes the flow of air or other gas through it.

DESCRIPTION OF THE PREFERRED EMBODIMENTS

Figure 1:
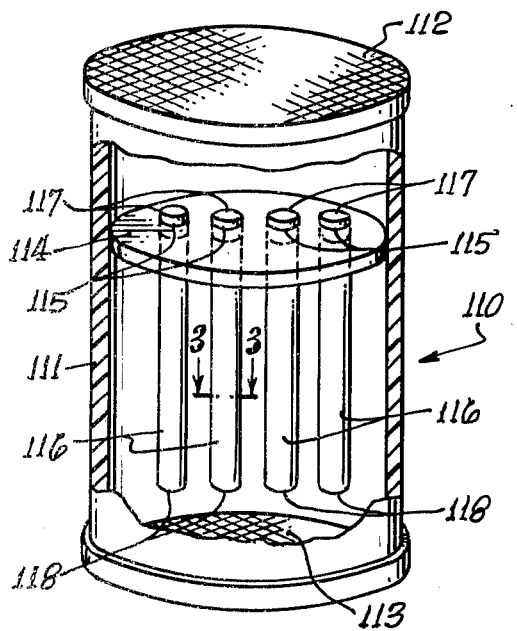
FIG. 1 is a perspective view, of the aerator of the present invention.

The aerator 110 of FIG. 1 is particularly adaptable for use in the neck of a flask. Although numerous other uses of the aerator are possible, this application will serve to describe the aerator and is not to be considered a limitation on its possible use. Aerator 110 has cylindrical wall 111 which may be made from a glass tube or other hollow member. A screen 112 may be positioned over the upper end of wall 111 and screen 113 is positioned over the lower end to protect the gas circulating members. Within the outside wall 111, a perforated plate 114 is sealed gas tight to the outside wall 111 and through the perforations 115, and sealed gas tight thereto pass the asymmetric gas pervious hollow members 116, open at their upper ends 117 and sealed gas tight at their lower ends 118.

Figure 3:
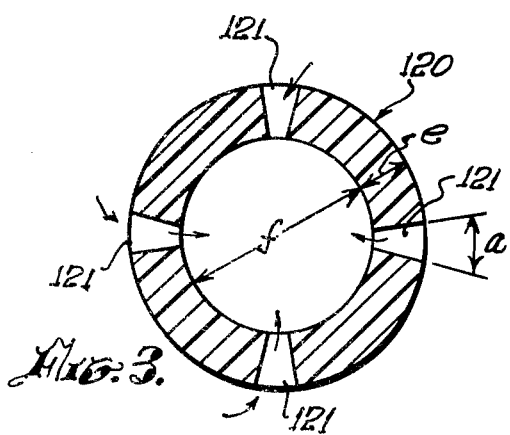
FIG. 3 is an enlarged cross sectional view of a hollow member of the aerator of FIG. 1.
Figure 4:
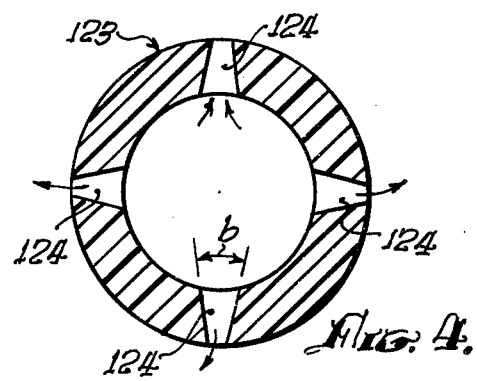
FIG. 4 is an enlarged cross sectional view of a hollow member of the aerator of FIG. 1 showing an alternate configuration of the holes.
Figure 5:
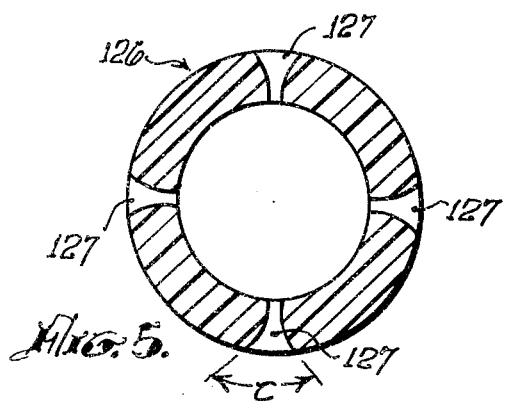
FIG. 5 is an enlarged cross sectional view of a hollow member of the aerator of FIG. 1 showing an alternate configuration of the holes.
Figure 6:
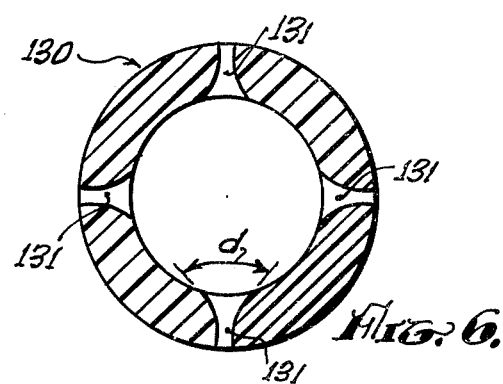
FIG. 6 is an enlarged cross sectional view of a hollow member of the aerator of FIG. 1 showing an alternate configuration of the holes.

As shown in FIG. 3, member 116 has a plurality of holes such as those indicated by reference character 121. Although the holes are depicted such that the smaller openings are all on the inside of the hollow member, the taper may be reversed as shown in FIG. 4 where all of the smaller openings of the holes, 124, are at the outside of the hollow member. Although the holes through the wall of the hollow member 116 and 123, FIGS. 3 and 4 are depicted as conical, the side walls of the holes may be concave or convex as viewed from the axis of the hole. Convex holes, 127 and 131 are depicted in FIGS. 5 and 6. A substantial majority of the tapered holes are aligned so that the larger openings of the holes are on one side of the wall of the hollow member and the smaller openings are on the opposite side of the wall of the hollow member.

The size and shape of the holes form an important aspect of the present invention. When the end openings of the tapered holes are approximately circular, then the mean diameter of the smaller of the two openings must be less than three times as great as the mean free path of the molecules of the gas in which the aerator is to operate at the given temperature and pressure. When the opening of the holes is not circular, the important dimension is the shortest distance across the opening which passes through the center of the opening in the curved plane of the surface of the wall of the hollow member. This dimension will be referred to herein as "the distance across the smaller opening". The mean free path of the molecules depends upon the composition, pressure and temperature of the gas and may be calculated by methods known to those skilled in the art. The distance across the smaller opening also must be greater than the minimum diameter of the given gas molecules. For air at 239° K. and 75 centimeters of mercury pressure, the mean free path of the molecules is about 0.09 microns. The distance across the smaller opening must therefore be less than 0.27 microns and greater than $3 \times 10^{-4}$ microns with $2 \times 10^{-3}$ microns being typical.

For pure oxygen at 293° K. at 7.5 centimeters of mercury pressure, the mean free path of oxygen molecules is about 1 micron. The distance across the small opening for an aerator for use under these conditions must be less than 3 microns and greater than $3 \times 10^{-4}$ microns. A typical diameter would be $2 \times 10^{-3}$ microns. For pure nitrogen at 278° K. and 0.75 centimeters of mercury, the mean free path is about 9 microns and the distance across the smaller opening must be less than 27 microns and greater than $3 \times 10^{-4}$ microns with about $2 \times 10^{-3}$ microns being preferred. For helium at 293° K. and 7.5 centimeters of mercury pressure the mean free path is about 3 microns. The distance across the smaller opening must be less than 9 microns and greater than $2 \times 10^{-4}$ microns with $2 \times 10^{-3}$ microns being preferred. For hydrogen at 203° K. and 750 centimeters of mercury pressure the mean free path is 0.03 microns. The distance across the smaller opening must be less that 0.09 microns and greater than $2 \times 10^{-4}$ microns with $2 \times 10^{-3}$ microns being preferred dimension. For carbon dioxide at 293° K. at 750 centimeters of mercury pressure the mean free path is 0.006 microns. The distance across the smaller opening must be less that 0.018 microns and greater than $3 \times 10^{-4}$ microns with $4 \times 10^{-3}$ microns being preferred. For air at 293° K. and 7500 centimeters of mercury, the mean free path equals $9 \times 10^{-4}$ microns. The distance across the smaller opening must be less than $2.7 \times 10^{-3}$ microns and greater than $3 \times 10^{-4}$ microns with $6 \times 10^{-4}$ microns being preferred. In addition to the above mentioned gases the system is useful with a wide variety including but not limited to carbon dioxide, hydrogen, helium, argon sulphur dioxide, a perhalogenated hydrocarbon, monochlorotrifluoromethane, hexafluorocyclobutane, dichlorodifluormethane, tetrafluoromethane and water vapor or steam.

The angular dimension between the opposite sides of the conical holes, 121 and 124 indicated in FIGS. 3 and 4 respectively by reference characters "a" and "b" should be between 2° and 150° with about 10° being preferred. When the opening is conical and in addition the larger opening is flared as shown by 127 and 131 in FIGS. 5 and 6, the angle of the flare, indicated by reference characters "c" and "d" should be between 10° and 180° with 150° being a preferred angular opening. While the exact angular dimension is not necessarily critical it is important that a substantial majority of the holes have their tapers in the same direction relative to the central axis of the hollow member. Substantially all the tapers in any given hollow member will be directed toward the central axis of the hollow member in unison, or the tapers will be directed away from the central axis in unison. The orientation of the tapers are depicted in FIGS. 3–6. With irregularly shaped holes it is difficult to quantify the size and shape and the hollow members containing irregularly shaped holes are best characterized by the hollow member's mean absolute effusional resistance coefficient, $\xi$, for a specified gas at a given pressure and temperature.

The wall thickness, "e" of the hollow member, shown in FIG. 3, should be less than about 3 millimeters with about 0.02 millimeters being preferred. Hollow member wall thickness such as 0.005 millimeters, 0.05 microns, and as small as 0.001 microns are contemplated.

The internal diameter of the hollow member, indicated by reference character "f", FIG. 3, should be less than about 10 centimeters with about 0.5 centimeters being preferred. Hollow members with an internal diameter such as 1 millimeter and 0.1 millimeter are contemplated. The internal perimeter of the hollow member perpendicular to the axis of the hollow hollow member, should be less than about 32 centimeters.

Figure 2:
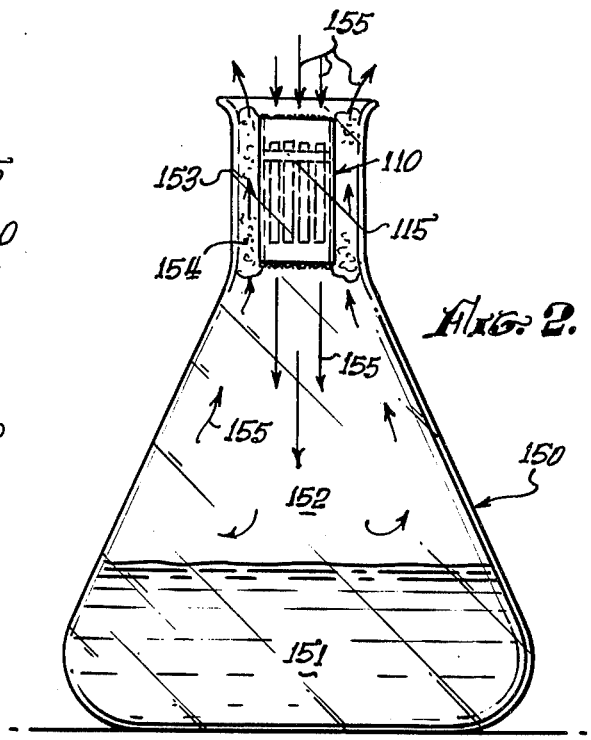
FIG. 2 is a side elevation showing the aerator of the present invention installed in the neck of the flask.
Figures 7, 8, 9:
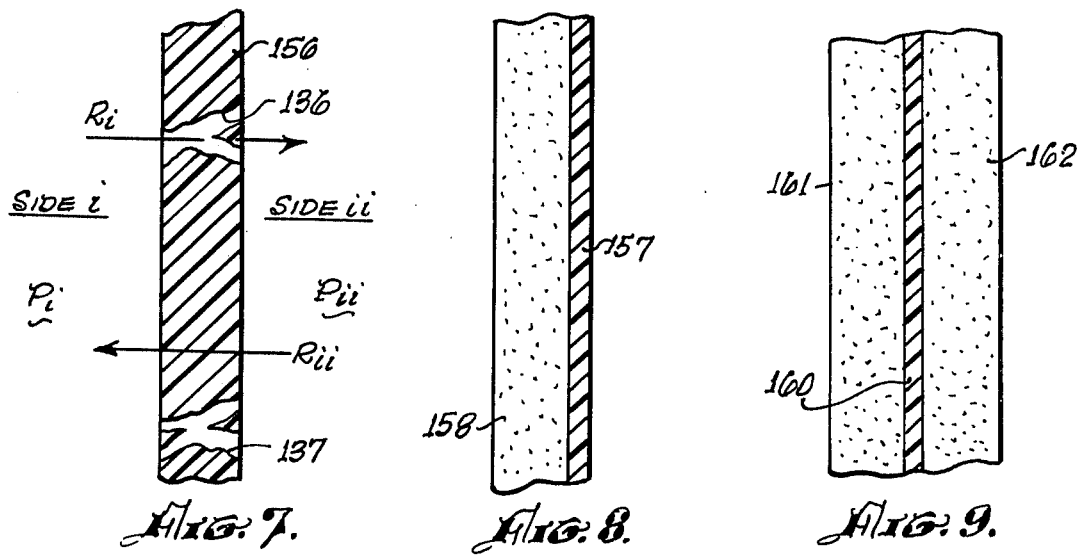
FIG. 7 is an enlarged fragmentary cross sectional side elevation of a wall of a hollow member of the aerator of the present invention.
FIG. 8 is an enlarged fragmentary cross sectional side elevation of a singly supported section of the wall of a hollow member of the aerator of the present invention.
FIG. 9 is an enlarged fragmentary cross sectional side elevation of a doubly supported section of the wall of a hollow member of the aerator of the present invention.

For use in the neck of a flask, the aerator is placed in the neck of flask 150 as shown in FIG. 2. The reaction medium 151 is held in the flask and the air or other gas 152 is above the reaction medium 151. Aerator 110 is held in neck 153 of flask 150 by a wad of cotton 154. The direction of air flow is indicated by arrows 155. As shown by arrows 155 the gas passes downwardly through aerator 110 and upwardly through cotton wad 154 where the orientation of the tapers through the wall of the hollow member corresponds to that shown in FIG. 4. When used in this specific application, surrounded by a wad of cotton or similar material as in FIG. 2, screens 112 and 113 of FIG. 1 may be used to protect the hollow members.

The number of hollow members utilized within the aerator, FIG. 1, may be varied considerably with one hollow member having some effect and a larger number of hollow members increasing the effectiveness of gas flow. Generally, the effect of number of members is additive. For example, the aerator could have 1, 5, 87, 2340 hollow members depending upon the desired effect. The aerator of the present invention will operate either quiescently or in a flask which is secured to a shaker table.

The number of holes in any one hollow member may be widely diverse depending upon the surroundings in which the hollow member is to operate. A hollow member having a single, tapered hole could be useful but generally a plurality of the holes is more useful. The number of holes should not, however, be such that adjacent holes intersect so that the geometry of the hole is destroyed. In other words, the number of holes should be such that there are actual separate holes although some limited overlapping is possible.

Referring to Equation (3) above, the mean absolute effusional resistance coefficient, $\xi$, should be greater than $1 \times 10^{-4}$ and preferably greater than $1 \times 10^{-2}$ and less than 2.0. A coefficient of about 0.1 is preferred for many practical applications. There are three different classes of openings which hollow members of the present invention may utilize: First, idealized holes through a wall of a hollow member, which is otherwise substantially impervious to the gas, where holes are identical in size and orientation. Such holes may be truncated pyramids where the cross section may be circular, eliptical, triangular, square, or polygonal. Secondly, the openings may be referred to as real holes where the holes are tapered and of distorted shape passing through a wall of a hollow member which is otherwise substantially impervious to the gas. Thirdly, the wall of the hollow member may be porous wherein the asymmetric holes through the wall of the hollow member are both highly branched and forked with the generally smaller openings on the first surface of the wall and the generally larger openings on the second surface of the wall. The orientation of the holes through the wall of the hollow member is such that a substantial majority of the smaller openings are all on the inside surface of the hollow member, or a substantial majority of the smaller openings are on the outside surface of the hollow member thereby maintaining the orientation of the tapers through the wall of the hollow member essentially all pointed outward from the center or inward toward the center of the hollow member. The wall of the hollow members may, of course, contain openings of any or all of the three above described types.

For many porous materials it is very difficult to measure the size of the openings on each side of the wall of the hollow member since the openings can vary in both size and shape. Further, the holes through the wall of the hollow member are not necessarily of simple and uniform dimensions. FIG. 7 depicts such a wall section having holes 136 and 137 passing through the wall. This porous hollow member as well as other gas pervious asymmetric hollow members can be characterized most readily by the above-described absolute effusional resistances, $R_i$ and $R_{ii}$ along with $\xi$, the hollow member's mean absolute effusional resistance coefficient. An isotropic, gas-pervious hollow member is one where $\xi = 0$ and the degree of anisotropy may be judged by the magnitude of the coefficient, $\xi$.

Generallly speaking, asymmetric pervious hollow members which show anisotropic effusional gas resistance properties, that is $\xi$ is different from zero, may be prepared in either of two ways or a combination of these two ways:

(a) asymmetry is incorporated during the formation of the hollow member itself as during the casting;

(b) the asymmetry is produced by modifying a symmetrical pervious hollow member.

The later modification (b), may be carried out by one of two processes (c) or (d) or a combination of them:

(c) the symmetrical holes through the wall of the hollow member are preferentially partially closed or filled on one side of the wall in preference to the opposite side by electroplating, acylation, esterification, etherification, vapor deposition, sputtering, heat treating, bending, stretching, radiation treatment or other process;

(d) the symmetrical holes through the wall of the hollow member are preferentially enlarged on one side of the wall in preference to those on the opposite side by such processes as etching, leching, hydrolysis, electromachining, stretching, bending, heat treatment, radiation treatment, machining, punching, or by other processes.

Hollow members may be made from sintered powders. When a compressed, finely-powdered solid is heated to a temperature somewhat below its melting point, the individual solid grains fuse together at their point of physical contact. This sintering, at the early stages, leaves large, interconnected voids and the mass is quite porous. As the temperature is increased, or the time of heating is increased, or both, the degree of sintering increases. The volume of the mass, upon increased sintering, decreases and the cross section of the void holes decreases in size.

Asymmetric sintered hollow members may be prepared by different degrees of sintering on the two sides of the wall of the hollow member such as would occur when the two sides were exposed to different sintering temperatures. If the starting powder was made up of particles of different sizes and the powder was classified by particle size across the wall of the hollow member and then sintered, the side having the larger particles would have larger holes, the side with the smaller particles would have smaller holes, and inside the wall of the hollow member holes would be of an intermediate size. Thus, generally tapered pores would be produced by such a classification of the particles prior to sintering. Such pores or openings may be highly interconnected and branched but the average mean diameter of the openings of the openings on the first surface are smaller than the average mean diameter on the second surface and the average mean diameter of the holes inside the member are of an intermediary average mean diameter. The material of the wall of the hollow members is a gas impervious continuous phase.

A wide variety of materials can be used for fabrication of hollow members. The material must be quite impermeable to gases and must be chemically and physically stable to the gas with which it is to be employed. Plastics such as nylon and polyethylene; metals such as aluminum and iron, ceramics such as glass and other silicates and the like are useful with consideration of corrosion resistance, temperature limitations and the like being adjusted to the environment in which the hollow members are to operate. The hollow member should be nonvolatile in the gaseous environment and the gas should be relatively insoluble in the hollow member. By "relatively insoluble" it is intended to mean that the gas will not dissolve in the hollow member to an extent sufficient to cause it to swell to an extent to weaken the hollow member or to change the size or shape of the openings to an extent to impair their function.

Equations 1 and 2 may be further understood by reference to FIG. 7 where the wall of the hollow member 156 has a first side referred to as side "i" in the drawing and a second side referred to as side "ii". The absolute effusional resistance from side "i" to side "ii" is referred to both in Equation (1) and in the drawings by $R_i$ and the absolute effusional resistance in the reverse direction is referred to as $R_{ii}$. From $R_i$ and $R_{ii}$ the mean absolute effusional resistance coefficient, $\xi$, may be calculated as shown in Equation (3) above.

Since the wall of the hollow member may be very thin, it is appropriate in many instances that it be supported by an inert base. The base must permit the relatively free flow of the gas. As shown in FIG. 8, a coarse gas-porous base 158 is affixed to wall of the hollow member 157. The support may be any inert, porous substance such as sintered glass. The wall of the hollow member may be double supported as shown in FIG. 9 where the wall of the hollow member 160 is supported by bases 161 and 162.

These asymmetric hollow members, 120, 123, 126, and 130 of FIGS. 3, 4, 5 and 6 respectively, 156 of FIG. 7, 157 of FIG. 8, and 160 of FIG. 9 in which the mean absolute effusional resistance coefficient, $\xi$, is greater than $10^{-4}$ and less than 2.0 under certain specified conditions of gas composition, pressure and temperature, may be used to fabricate activating units for use as aerators.

While the use of the activating unit of the present invention as an aerator has been discussed as being particularly useful in the neck of a flask, the invention has far greater applications. The activating unit or activating units, may be used in any conduit which has gas impermeable walls. Such an aerator is shown as 172 in FIG. 10 where it is sealed, gas tight, into conduit 173 connecting tanks 170 and 171. The conduit 174 provides for the return circulation. The hollow member in the aerator, 172 in FIG. 10 forms a gas-tight barrier across conduit 173 and thereby prevents the unrestricted free flow of gas through the conduit 173. The anisotropy of the effusional resistance of the hollow member to the gas urges the gas therethrough and through the conduit 173.

Figure 10:
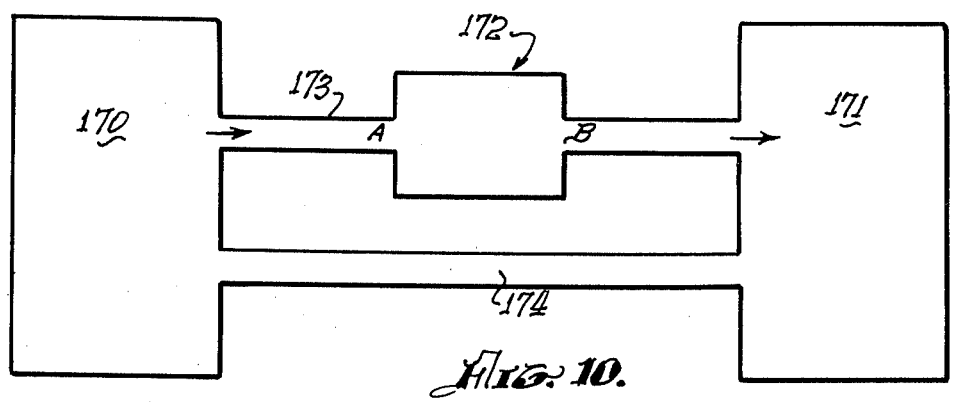
FIG. 10 is a side elevation of a pair of tanks connected by a pair of conduits, one of which contains an aerator of the present invention.
Figure 11:
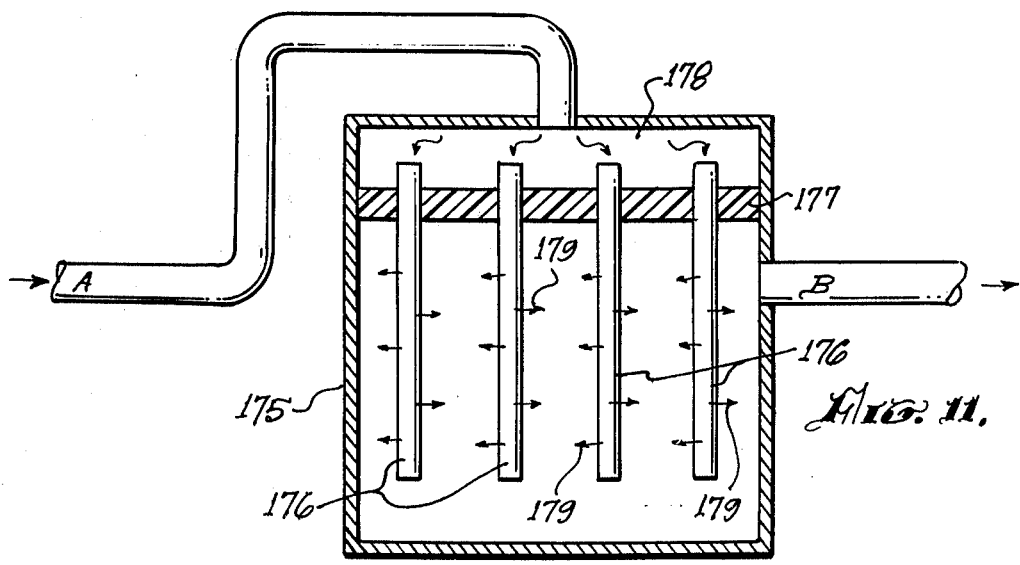
FIG. 11 is a detailed cross sectional view of a first configuration of the aerator of the present invention.
Figure 12:
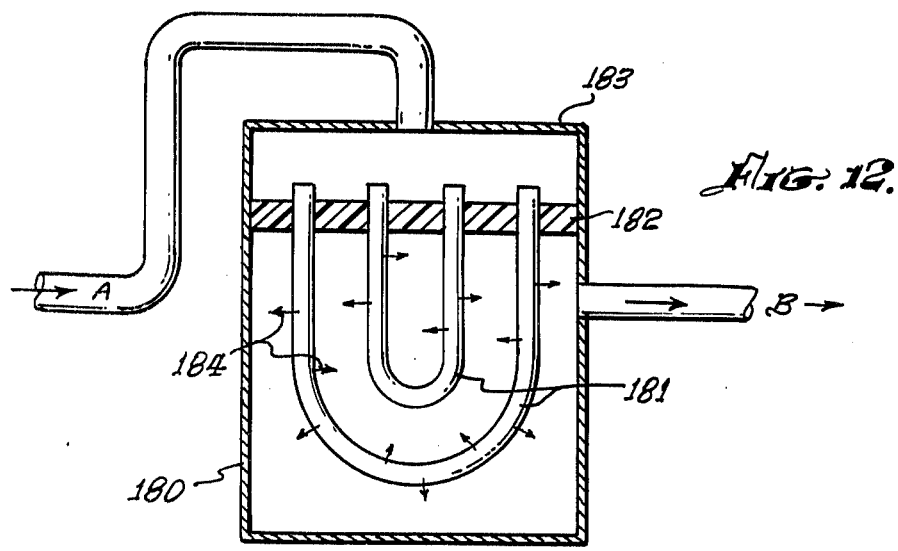
FIG. 12 is a detailed cross sectional view of an alternate configuration of the aerator of the present invention.
Figure 13:
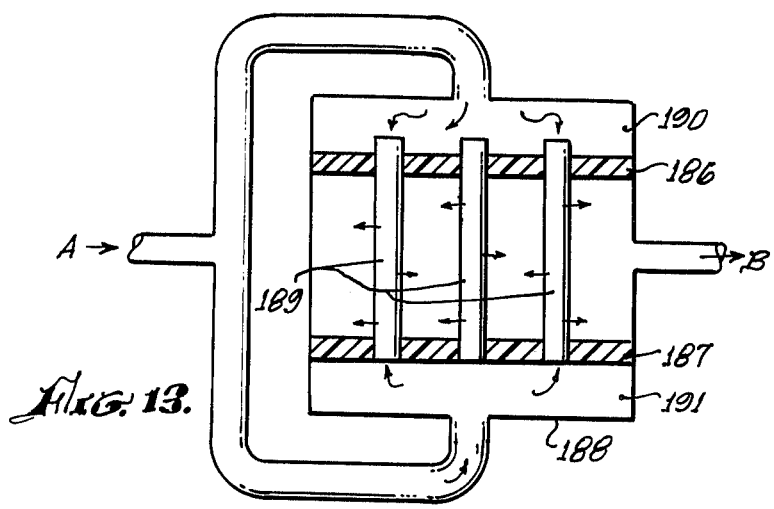
FIG. 13 is a detailed cross sectional view of an alternate configuration of the aerator of the present invention.

Illustrative configurations of the aerator 172 of FIG. 10 are depicted in FIGS. 11-13. In FIG. 11 a plurality of members, 176, sealed gas tight at the lower end, are sealed gas tight through a perforated plate 177 into the gas distributor 178. The perforated plate, 177, forms a gas-tight seal with the body of the aerator 175. The gas which passes between A and B must pass through the walls of the hollow members 176. The direction of the net gas flow by effusion through the walls of the hollow members 176 is indicated by the arrows 179 at the members 176 of FIG. 11. Such direction of flow results when the holes have their smaller openings on the outside of the member such as those shown in FIGS. 4 and 6 of the drawings. When the tapers of the holes through the hollow members 176 are substantially all in the reverse direction so that the smaller openings of the holes are on the inside of the members 176, then the gas will be urged to flow from the outside toward the inside of the hollow member, and the net gas flow will be from B to A in FIG. 11.

In FIG. 12 a plurality of members, 181, are sealed gas-tight through a perforated otherwise gas impervious partition 182 which is sealed gas-tight to the chamber 180. The gas distributor 183, connects all of the ends of the hollow members 181. When the holes through the hollow members 181 have a substantial majority of their smaller openings at the outside of the hollow members, the net flow of the gas will be in the direction of the arrows 184 in FIG. 12. When the holes through the hollow members have a substantial majority of their openings at the inside of the hollow members, the net flow of the gas will be in the direction opposite to that indicated by the arrows in FIG. 12.

In FIG. 13 a plurality of members, 189 are sealed gas-tight through two perforated, otherwise gas-impervious partitions, 186 and 187, which are in turn sealed gas tight to the body of the chamber 188. The only passage for the flow of gas between the points A and B of FIG. 13 is through the walls of the hollow members 189. The gas distributors 190 and 191 are connected to the common conduit at A.

A number of aerator units such as those depicted in FIGS. 11–13 may be connected together in series, or in parallel, or in a combination of the two. Generally, multiple units will increase the gas flow.

The number of hollow members used in a given aerator unit may be only one but usually will be numerous are even quite large such as 5, 80, 400 or 12,000. The number of aerator units used together may be only one but usually, depending upon the requirements, many will be used together such as 40, 800 or even 30,000.

Figure 14:
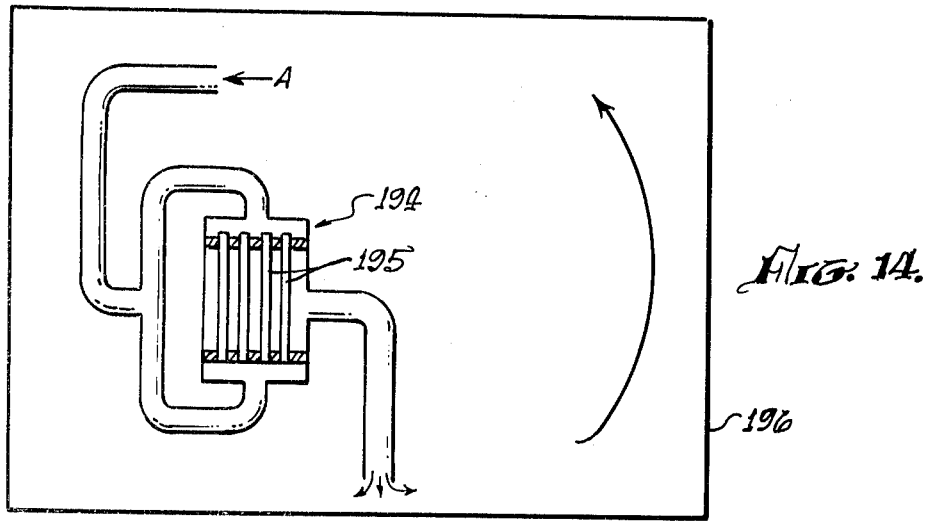
FIG. 14 is a side elevation of a room having a conduit containing an aerator of the present invention.

FIG. 14 illustrates how this device may be used as a circulator to induce the circulation of air or other gas. An aerator, 194, of the type depicted in FIG. 13 is placed at the bottom of a room or a tank, 196, and a conduit is extended from the aerator unit 194 to the top of the enclosure. The gas is drawn in at A, effuses through the hollow members 195, as shown by the arrows and is discharged at B. The mean absolute effusional resistance coefficient, $\xi$, of the walls of the hollow members, 195, is greater $10^{-4}$ and less than 2.0 at the temperature and pressure of the gas being circulated.

The present embodiments of this invention are thus to be considered in all respects as illustrative and not restrictive, the scope of the invention being indicated by the foregoing description. All changes which come within the meaning and range of equivalency of the claims therefore are intended to be embraced therein.

I claim:
1. A gas circulating system comprising:
   a gas;
   at least one hollow member of a relatively gas impermeable material, positionable within a gas impervious chamber, and wherein said chamber has two sets of conduits attached to it so as to form a gas-tight seal between the conduits and the chamber so that gas may flow between the chamber and said conduits unimpaired, and wherein the first set of conduits has at least one unit and the second set of conduits has at least one unit, and said hollow member is open on at least one end, and wherein all of the open ends of the hollow member are connected, gas tight, to the first set of conduits so as to form a barrier to the unrestricted flow of gas between the said first set of conduits and the said second set of conduits, and wherein the individual conduits making up any one given set of said conduits may be interconnected with other conduits to the same set outside the chamber, and wherein the open ends of at least two of said hollow members may be interconnected, gas tight, inside said chamber, by a channel with gas impervious walls except where the open ends of said hollow member connect to the channel, and except where at least one unit of said first set of conduits is connected, gas tight, to said channel so as to form an unimpaired passage for the flow of gas between the inside of said hollow member and the said first set of conduits and so that the only passage for the flow of gas between the said first set of conduits and the said second set of conduits is through the wall of the said hollow member, and wherein the wall of said hollow member has a thickness of less than about 3 millimeters and greater than about 0.001 micron, and wherein said wall contains a multiplicity of uniform tapered holes passing from first surface of the wall of said hollow member to the second surface of the wall of said hollow member, and wherein a substantial majority of the tapers of the holes are aligned so that the smaller openings are on one of the continuous surfaces of the wall and the larger openings are on the opposite continuous surface of the wall, and wherein the distance across the smaller openings of the holes is less than three times the mean free path of the molecules of the gas which is to be employed with this gas circulating system, at its operating temperature and pressure, and larger than the minimum diameter of said gas molecules, and wherein the hollow member is less than about 10 centimeters in diameter when extended in the form of a circular cylinder, and wherein the inside perimeter of said hollow member, perpendicular to the axis of said hollow member, is less than about 32 centimeters, and wherein the said hollow member, the said chamber, and the said conduits are all both chemically and physically stable to the gas which is to be employed with this gas circulating system, and wherein the material of said hollow member, the said chamber and the said conduits are all relatively nonvolatile under the conditions of temperature and gas pressure which are to be employed with this gas circulating system, and wherein the mean absolute effusional resistance coefficient, $\xi$, of the wall of said hollow member, is greater than $10^{-4}$ and less than 2.0 in the gas to be circulated, and whereby when said hollow member is positioned within said chamber so as to separate the said two sets of conduits attached to said chamber so as to form a gas-tight barrier to the flow of gas between the first said set of conduits and the second said set of conduits, and said chamber and said hollow member and said set of conduits are all filled with said gas, at operating temperature and pressure the gas is urged through said hollow member and through said chamber and through said first set of conduits and through said second set of conduits.

2. The circulating system of claim 1 wherein the tapered holes are uniform and the angular dimension between the opposite sides of the holes is between 2° and 150°.

3. The circulating system of claim 2 wherein said angle is about 10°.

4. The circulating system of claim 1 wherein said tapered holes are conical in shape.

5. The system of claim 1 wherein said system has one of said hollow member.

6. The system of claim 1 wherein said system has a plurality of said hollow members.

7. The system of claim 6 wherein said system has five of said hollow members.

8. The system of claim 1 wherein the wall of the hollow member of said system has a thickness of about 0.02 millimeters.

9. The system of claim 1 wherein the mean absolute effusional resistance coefficient, $\xi$, is approximately 0.1.

10. The system of claim 1 wherein said tapered holes are conical in shape and in addition flared at the end with the larger opening wherein the angle between the opposite sides of the flare where it meets the surface of the hollow member is between 10° and 180°.

11. The system of claim 10 wherein said angle is about 150°.

12. The system of claim 1 designed for use in air wherein the mean distance across the opening at the smaller end of the hole is about 0.002 microns.

13. The system of claim 1 wherein said hollow member is supported by a coarse gas-pervious base on one side.

14. The system of claim 1 wherein said hollow member is supported by a coarse gas-pervious base on both sides thereof.

15. The system of claim 14 wherein said coarse gas-pervious base is sintered glass.

16. The system of claim 14 wherein said coarse gas-pervious bases are sintered glass.

17. The system of claim 1 wherein the gas is air.

18. The system of claim 1 wherein the gas is nitrogen.

19. The system of claim 1 wherein the gas is carbon dioxide.

20. The system of claim 1 wherein the gas is hydrogen.

21. The system of claim 1 wherein the gas is helium.

22. The system of claim 1 wherein the gas is argon.

23. The system of claim 1 wherein the gas is sulphur dioxide.

24. The system of claim 1 wherein the gas is a perhalogenated hydrocarbon.

25. The system of claim 24 wherein the gas is monochlorotrifluoromethane.

26. The system of claim 24 wherein the gas is hexafluorocyclobutane.

27. The system of claim 24 wherein the gas is dichlorodifluoromethane.

28. The system of claim 24 wherein the gas is tetrafluoromethane.

29. The system of claim 1 wherein the gas is water in the vapor state.

30. The circulating system of claim 1 wherein the said hollow member has an internal perimeter, perpendicular to the axis of the hollow member, of 3 millimeters.

31. The circulating system of claim 1 wherein a substantial majority of the smaller openings of the tapered holes, through the wall of the hollow member, are on the inside surface of the wall.

32. The circulating system of claim 1 wherein a substantial majority of the smaller openings of the tapered holes, through the wall of the hollow member, are on the outside surface of the wall.

33. The circulating system of claim 1 wherein the set of inlet conduit ports has one member.

34. The circulating system of claim 1 wherein the set of outlet conduit ports has one member.

35. The circulating system of claim 1 wherein the said hollow member has a plurality of end openings.

36. The circulating system of claim 1 wherein the said hollow member has one end openings.

37. The circulating system of claim 1 wherein the said hollow member has two end openings.

38. A gas circulating system comprising:
a gas;
at least one hollow member of a relatively gas impermeable material, positionable within a gas impervious chamber, and wherein said chamber has two sets of conduits attached to it so as to form a gas-tight seal between the conduits and the chamber so that gas may flow between the chamber and said conduits unimpaired, and wherein the first set of conduits has at least one unit and the second set of conduits has at least one unit, and said hollow member is open on at least one end, and wherein all of the open ends of the hollow member are connected, gas tight, to the first set of conduits so as to form a barrier to the unrestricted flow of gas between the said first set of conduits and the said second set of conduits, and wherein the individual conduits making up any one given set of said conduits may be interconnected with other conduits to the same set outside the chamber, and wherein the open ends of at least two of said hollow members may be interconnected, gas tight, inside said chamber, by a channel with gas impervious walls except where the open ends of said hollow member connect to the channel, and except where at least one unit of said first set of conduits is connected, gas tight, to said channel so as to form an unimpaired passage for the flow of gas between the inside of said hollow member and the said first set of conduits and so that the only passage for the flow of gas between the said first set of conduits and the said second set of conduits is through the wall of said hollow member, and wherein the wall of said hollow member has a thickness of less than about 3 millimeters and greater than about 0.001 micron, and wherein said wall contains a multiplicity of generally irregular tapered holes passing from first surface of the wall of said hollow member to the second surface of the wall of said hollow member, and wherein a substantial majority of the tapers of the holes are aligned so that the smaller openings are on one of the continuous surfaces of the wall and the larger openings are on the opposite continuous surface of the wall, and wherein the distance across the smaller openings of the holes is less than three times the mean free path of the molecules of the gas which is to be employed with this gas circulating system, at its operating temperature and pressure, and larger than the minimum diameter of said gas molecules, and wherein the hollow member is less than about 10 centimeters in diameter when extended in the form of a circular cylinder, and wherein the inside perimeter of said hollow member, perpendicular to the axis of said hollow member, is less than about 32 centimeters, and wherein the said hollow member, the said chamber, and the said conduits are all both chemically and physically stable to the gas which is to be employed with this gas circulating system, and wherein the material of said hollow member, the said chamber and the said conduits are all relatively nonvolatile under the conditions of temperature and gas pressure which are to be employed with this gas circulating system, and wherein the mean absolute effusional resistance coefficient, $\xi$, of the wall of said hollow member, is greater than $10^{-4}$ and less than 2.0 in the gas to be circulated, and whereby when said hollow member is positioned within said chamber so as to separate the said two sets of conduits attached to said chamber so as to form a gas-tight barrier to the flow of gas between the first said set of conduits and the second said set of conduits, and said chamber and said hollow member and said sets of conduits are all filled with said gas at operating temperature and pressure the gas is urged through said hollow member and through said chamber and through said first set of conduits and through said second set of conduits.

39. The circulating system of claim 38 wherein the irregular tapered holes are not uniform and the average mean value of the angular dimension between the opposite sides of the holes is between 2° and 150°.

40. The circulating system of claim 39 wherein the average mean value of the said angular dimension is about 10°.

41. The system of claim 38 wherein said system has one of said hollow members.

42. The system of claim 38 wherein said system has a plurality of said hollow members.

43. The system of claim 42 wherein said system has five of said hollow members.

44. The system of claim 38 wherein the mean absolute effusional resistance coefficient, $\xi$, is approximately 0.1.

45. The system of claim 38 wherein waid wall of the hollow member has a thickness of about 0.02 millimeters.

46. The system of claim 38 wherein said irregular, generally tapered holes are in addition flared at the end with the larger opening wherein the average mean value of the angle between the opposite sides of the flare where the flare meets the surface of the hollow member is between 10° and 180°.

47. The system of claim 46 wherein the average mean value of the said angle is about 150°.

48. The system of claim 38 designed for use with air wherein the mean distance across the opening at the smaller end of the hole is about 0.002 microns.

49. The system of claim 38 wherein the wall of the hollow member has a thickness of about 0.02 millimeters.

50. The system of claim 38 wherein said hollow member is supported by a coarse gas-pervious base on one side.

51. The system of claim 50 wherein said coarse gas-pervious base is sintered glass.

52. The system of claim 38 wherein said hollow member is supported by a coarse gas-pervious base on both sides thereof.

53. The system of claim 52 wherein said coarse gas-pervious bases are sintered glass.

54. The system of claim 38 wherein the gas is air.

55. The system of claim 38 wherein the gas is nitrogen.

56. The system of claim 38 wherein the gas is carbon dioxide.

57. The system of claim 38 wherein the gas is hydrogen.

58. The system of claim 38 wherein the gas is helium.

59. The system of claim 38 wherein the gas is argon.

60. The system of claim 38 wherein the gas is sulphur dioxide.

61. The system of claim 38 wherein the gas is a perhalogenated hydrocarbon.

62. The system of claim 61 wherein the gas is monochlorotrifluoromethane.

63. The system of claim 61 wherein the gas is hexafluorocyclobutane.

64. The system of claim 61 wherein the gas is dichlorodifluoromethane.

65. The system of claim 61 wherein the gas is tetrafluoromethane.

66. The system of claim 38 wherein the gas is water in the vapor state.

67. A gas circulating system comprising:
a gas;
at least one hollow member of a relatively gas impermeable material, positionable within a gas impervious chamber, and wherein said chamber has two sets of conduits attached to it so as to form a gas-tight seal between the conduits and the chamber so that gas may flow between the chamber and said conduits unimpaired, and wherein the first set of conduits has at least one unit and the second set of conduits has at least one unit, and said hollow member is open on at least one end, and wherein all of the open ends of the hollow member are connected, gas tight, to the first set of conduits so as to form a barrier to the unrestricted flow of gas between the said first set of conduits and the said second set of conduits, and wherein the individual conduits making up any one given set of said conduits may be interconnected with other conduits to the same set outside the chamber, and wherein the open ends of at least two of said hollow members may be interconnected, gas tight, inside said chamber, by a channel with gas impervious walls except where the open ends of said hollow member connect to the channel, and except where at least one unit of said first set of conduits is connected, gas tight, to said channel so as to form an unimpaired passage for the flow of gas between the inside of said hollow member and the said first set of conduits and so that the only passage for the flow of gas between the said first set of conduits and the said second set of conduits is through the wall of the said hollow member, and wherein the wall of said hollow member has a thickness of less than about 3 millimeters and greater than about 0.001 micron, and contains a multiplicity of highly interconnected and branched holes which pass from the first surface of the wall of the hollow member to the second surface of the wall of the hollow member, and wherein the average means diameter of the openings of the holes on the first surface are smaller than the average mean diameter of the openings of the holes on the second surface, and wherein the average mean diameter of the holes inside of the member are of an intermediary average mean diameter between the average mean diameter of the openings of the holes on the two opposite sides of the wall of the hollow member, and wherein the solid material of the hollow member consists of one relatively gas impervious continuous phase through which the network of holes pass, and wherein the average mean diameter of the openings of the holes in the first surface is greater than the average mean diameter of the molecules of the gas employed in the gas circulating system and less than three times the mean free path of the said gas molecules under the operating conditions of this gas circulating system, and wherein the hollow member is less than about 10 centimeters in diameter when extended in the form of a circular cylinder, and wherein the inside perimeter of said hollow member, perpendicular to the axis of said hollow member, is less than about 32 centimeters, and wherein the said hollow member, the said chamber, and the said conduits are all both chemically and physically stable to the gas which is to be employed with this gas circulating system, and wherein the material of said hollow member, the said chamber and the said conduits are all relatively nonvolatile under the conditions of temperature and gas pressure which are to be employed with this gas circulating system, and wherein the mean absolute effusional resistance coefficient, $\xi$, of the wall of said hollow member, is greater than $10^{-3}$ and less than 2.0 in the gas to be circulated, and whereby when said hollow member is positioned within said chamber so as to separate the said two sets of conduits attached to said chamber so as to form a gas-tight barrier to the flow of gas between the first said set of conduits and the second said set of conduits, and said chamber and said hollow member and said sets of conduits are all filled with said gas at operating temperature and pressure the gas is urged through said hollow member and through said chamber and through said first set of conduits and through said second set of conduits.

68. The system of claim 67 wherein said system has one said hollow member.

69. The system of claim 67 wherein said system has a plurality of said hollow members.

70. The system of claim 69 wherein said system has five of said hollow members.

71. The system of claim 67 wherein the wall of the hollow member of said system has a thickness of about 0.02 millimeters.

72. The system of claim 67 wherein the mean absolute effusional resistance coefficient, $\xi$, is approximately 0.1.

73. The system of claim 67 designed for use in air wherein the average mean distance across the openings at the smaller end of the hole is about 0.002 microns.

74. The system of claim 67 wherein said hollow member is supported by a coarse gas-pervious base on one side.

75. The system of claim 74 wherein said coarse gas-pervious base is sintered glass.

76. The system of claim 67 wherein said hollow member is supported by a coarse gas-pervious base on both sides thereof.

77. The system of claim 76 wherein said coarse gas-pervious bases are sintered glass.

78. The system of claim 67 wherein the gas is air.

79. The system of claim 67 wherein the gas is nitrogen.

80. The system of claim 67 wherein the gas is carbon dioxide.

81. The system of claim 67 wherein the gas is hydrogen.

82. The system of claim 67 wherein the gas is helium.

83. The system of claim 67 wherein the gas is argon.

84. The system of claim 67 wherein the gas is sulphur dioxide.

85. The system of claim 67 wherein the gas is a perhalogenated hydrocarbon.

86. The system of claim 85 wherein the gas is monochlorotrifluoromethane.

87. The system of claim 85 wherein the gas is hexafluorocyclobutane.

88. The system of claim 85 wherein the gas is dichlorodifluoromethane.

89. The system of claim 85 wherein the gas is tetrafluoromethane.

90. The system of claim 67 wherein the gas is water in the vapor state.

91. The circulating system of claim 67 wherein the said hollow member has an internal perimeter, perpendicular to the axis of the hollow member, of 3 millimeters.

92. The circulating system of claim 67 wherein a substantial majority of the smaller openings of the tapered holes, through the wall of the hollow member, are on the inside surface of the wall.

93. The circulating system of claim 67 wherein a substantial majority of the smaller openings of the tapered holes, through the wall of the hollow member, are on the outside surface of the wall.

94. The circulating system of claim 67 wherein the set of inlet conduit ports has one member.

95. The circulating system of claim 67 wherein the set of outlet conduit ports has one member.

96. The circulating system of claim 67 wherein the said hollow member has a plurality of end openings.

97. The circulating system of claim 67 wherein the said hollow member has one end opening.

98. The circulating system of claim 67 wherein the said hollow member has two end openings.

* * * * *